ated Feb. 5, 1985

United States Patent [19]
Kurihara et al.

[11] Patent Number: 4,497,847
[45] Date of Patent: Feb. 5, 1985

[54] PROCESS FOR COATING SOLID PHARMACEUTICAL PREPARATIONS AND COATED PREPARATIONS THUS OBTAINED

[75] Inventors: Kozo Kurihara; Izuo Ichikawa; Hisanori Nakane; Yoshihiko Ikegami, all of Hiromachi, Japan

[73] Assignee: Sankyo Company, Limited, Tokyo, Japan

[21] Appl. No.: 540,718

[22] Filed: Oct. 11, 1983

[30] Foreign Application Priority Data

Oct. 12, 1982 [JP] Japan ................. 57-177595

[51] Int. Cl.³ .............................................. A61K 9/38
[52] U.S. Cl. ....................................... 427/3; 424/35; 424/33
[58] Field of Search ................ 424/35, 33; 427/3

[56] References Cited

U.S. PATENT DOCUMENTS 3,149,040  9/1964  Jeffries .................................. 424/35
3,959,540  5/1976  Leiberich ............................. 424/33
4,385,078  5/1983  Onda ...................................... 427/3

OTHER PUBLICATIONS

WO 80/00659, Apr. 17, 1980.

*Primary Examiner*—Sam Silverberg
*Attorney, Agent, or Firm*—Frishauf, Holtz, Goodman & Woodward

[57] ABSTRACT

A plasticizer for film-forming enteric polymers to be used in coating solid pharmaceutical preparations comprises a monoester or diester or both of glycerol with a saturated aliphatic carboxylic acid having from 6 to 10 carbon atoms. This is particularly useful for coating preparations from aqueous suspensions.

14 Claims, 1 Drawing Figure

PROCESS FOR COATING SOLID PHARMACEUTICAL PREPARATIONS AND COATED PREPARATIONS THUS OBTAINED

BACKGROUND TO THE INVENTION

The present invention relates to a process for coating solid pharmaceutical preparations using an aqueous coating material including an enteric polymer and a specific class of plasticizer for the polymer. The invention also relates to the coated preparations thus obtained.

There are many reasons why solid pharmaceutical preparations need to be coated with an essentially continuous film. One such reason may be that the pharmaceutical is intended to pass through the stomach unaffected, only to be released in the intestines—in such a case, the pharmaceutical would be coated with a "enteric" coating which is impermeable to gastric juices, thus protecting the pharmaceutical from dissolution in the stomach. Other reasons for coating pharmaceutical preparations may be the need to protect the preparation from the effect of atmospheric oxygen or moisture. Nowadays, high polymers are most commonly used to produce the coating film.

Normally, however, the film-forming polymer is incapable of forming a suitably continuous film by itself and it is necessary to incorporate a plasticizer into the coating composition. Although, the nature of such plasticizers is restricted by the requirement that they should be safe to administer to human beings, a very wide range of compounds has been proposed for use as the plasticizer in such coating compositions and many of the compounds proposed are used in actual practice. For example, PCT publication No. 80/00659 suggests the use of propylene glycol, glycerol, glyceryl triacetate, polyethylene glycol, triethyl citrate, tributyl citrate, diethyl phthalate and dibutyl phthalate. Glycerides of higher fatty acids (particularly stearic acid) are proposed for use as plasticizers in "Coating of Pharmaceuticals", in the Modern Pharmaceutical Preparation Technology Series No. 1, published by Nihon Kogyogijutsu Renmei (The Industrial Technology League of Japan), 1969, and in Remington's Pharmaceutical Science, 14th Edition, Mack Publishing Co., 1970. One of the plasticizers illustrated in Japanese Patent Application Kokai (i.e. as laid open to public inspection) No. 104823/81 is described as "monoglyceride", but it is clear from the context of that specification and from the prior art that the "monoglyceride" referred to is a glyceride of a higher fatty acid.

Normally, the coating composition will be applied to the solid preparation as a solution or suspension in an appropriate liquid medium which, after application, is then removed, leaving the desired polymer film. Of course, the nature of the liquid medium chosen may constrain the choice of plasticizer or, conversely, the plasticizer chosen may place constraints upon the choice of medium. In general, the coating composition may be applied in any one of the following four systems:

(1) A system in which both the high polymer and the plasticizer are soluble in the liquid coating vehicle;
(2) a system in which the high polymer is soluble in the coating vehicle but in which the plasticizer is insoluble;
(3) a system in which the high polymer is insoluble in the coating vehicle, but the plasticizer is soluble; and
(4) a system in which both the high polymer and the plasticizer are insoluble in the coating vehicle.

In systems (1)–(3), the coating vehicle has the effect of enhancing phase solubility between the plasticizer and the film-forming high polymer and, in this case, even plasticizers having relatively low plasticizing ability will provide the film with adequate plasticity. On the other hand, where both the high polymer and the plasticizer are insoluble in the coating vehicle, as in system (4), it is necessary to employ a higher grade of plasticizer, in order to ensure that the film has adequate plasticity. Thus, although plasticizers useful in system (4) are generally equally useful in systems (1)–(3), plasticizers useful in systems (1)–(3) are not necessarily useful as plasticizers in system (4).

Most compounds known for use as organic solvents are easily capable of dissolving such organic materials as high polymers and plasticizers, and a wide variety of compounds are known for use as organic solvents. Accordingly, when the coating vehicle is an organic solvent it rarely forms a system of type (4). Systems of type (4) usually contain water as the coating vehicle, although, for a number of reasons, such water-based systems have been relatively rare in practice. However, in recent years, various considerations, such as safety, economics and the avoidance of pollution, have made systems based upon organic solvents relatively less desirable than aqueous systems and systems of type (4) using water as the coating vehicle are beginning to be of practical importance.

Particularly important from the industrial point of view are enteric coating agents using water as the coating vehicle. High polymers employed for enteric coatings should be essentially insoluble in water in order to fulfill their function. Moreover, the plasticizer employed should be essentially insoluble in water. If the plasticizer is very soluble in water, the film produced with such a plasticizer becomes permeable to gastric juices, so that an enteric coating is not achieved and the pharmaceutical may be released in the stomach or inactivated or decomposed by permeated gastric juices. It is, therefore, necessary that the plasticizer employed should be essentially insoluble in water, at least, to the extent that it does not completely dissolve in water.

On the other hand, we have surprisingly found that the plasticizer should not be completely insoluble in water when used in a system of type (4), since a completely insoluble plasticizer will not allow a continuous film to be produced.

A further constraint upon the choice of plasticizer is that, as explained above, for an enteric coating using water as the coating vehicle in a system of type (4), a relatively high quality plasticizer is needed and such plasticizers are highly desired by the pharmaceutical industry.

We have now found that the mono- and di-glycerides of saturated aliphatic carboxylic acids having from 6 to 10 carbon atoms ("intermediate fatty acids"), but surprisingly not the corresponding triglycerides, meet the requirements outlined above and that they are especially valuable in that they can be used in systems of the type (4).

BRIEF SUMMARY OF INVENTION

Accordingly, in one aspect, the present invention provides a process for coating a solid pharmaceutical preparation, in which an aqueous suspension of a film-forming enteric polymer and a plasticizer therefor is applied to a surface of said preparation and the aqueous phase is removed, wherein the plasticizer is selected from monoesters, diesters and mixtures thereof of glycerol with a saturated aliphatic carboxylic acid having from 6 to 10 carbon atoms.

In another aspect, the invention provides a solid pharmaceutical preparation having a coating comprising a film-forming enteric polymer and a plasticizer therefor, wherein the plasticizer is selected from monoesters, diesters and mixtures thereof of glycerol with a saturated aliphatic carboxylic acid having from 6 to 10 carbon atoms.

We have found that these mono and diesters, but not the triesters, are highly effective as plasticizers for film-forming polymers and thus are particularly valuable for use with aqueous systems although, as explained above, such plasticizers are also effective in organic solvent-based systems. This contrasts with the behaviour of the similar monoesters and diesters of glycerol with higher and lower aliphatic carboxylic (fatty) acids which, although effective in organic solvent-based systems, are ineffective in aqueous systems.

DETAILED DESCRIPTION OF INVENTION

Figure 1:
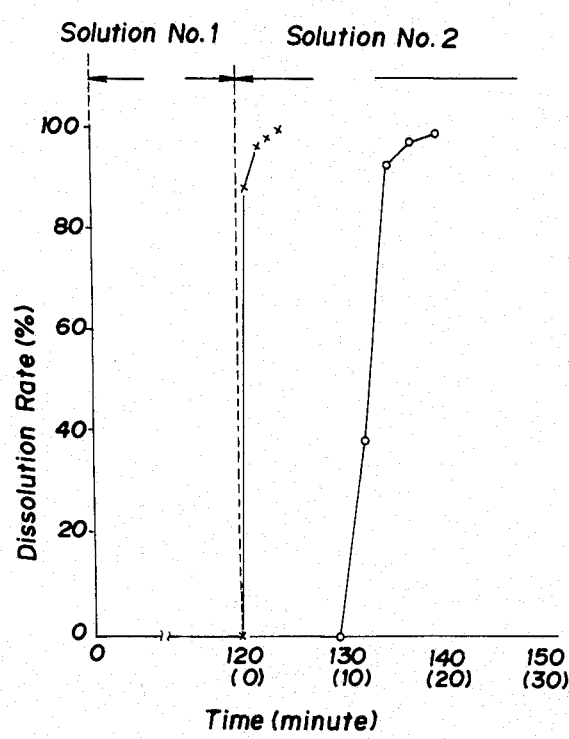

The plasticizers employed in the present invention are monoesters and diesters of glycerol with saturated aliphatic carboxylic acids having from 6 to 10 carbon atoms. Examples of such acids include hexanoic acid, 4-methylpentanoic acid, heptanoic acid, 5-methylhexanoic acid, octanoic acid, 6-methylheptanoic acid, nonanoic acid, decanoic acid and 8-methylnonanoic acid. Of these acids, the straight chain acids are preferred, particularly those having an even number of carbon atoms, i.e. hexanoic acid, octanoic acid and decanoic acid.

Where a diester of glycerol is employed, the two fatty acid moieties on each molecule may be the same or different, although they are preferably the same, as such esters are easier to prepare. Mixtures of esters (which may be monoesters and/or diesters) with different fatty acids may also be employed.

In general, fatty acid esters of glycerol are mixtures of the monoester, the diester and the triester. As already noted, the triesters do not achieve good results; however, the presence in the plasticizer of some triester can be tolerated, provided that the amount is not such that the properties of the triester predominate and interfere with the good plasticizing effect achieved by the monoesters and/or diesters. In practice, when preparing esters of glycerol, the three possible esters (the monoester, the diester and the triester) are formed together; the balance between the three esters will depend upon the manufacturing conditions and, in particular, upon the proportions of reagents. The balance between the monoester and diester is not critical to the present invention and these two esters may be present in the plasticizer in any proportion; however, the manufacturing process is preferably carried out under such conditions as to minimize the formation of triester, although this cannot be prevented completely. If desired, the triester may be removed from the product by standard chemical techniques and also, if desired, the monoester and diester may be separated from each other; however, these expedients are not normally commercially advantageous and accordingly a mixture of the three esters in varying proportions will be used.

Any conventional film-forming enteric polymer may be used in the present invention. Examples include: carboxymethylethylcellulose, cellulose acetate phthalate, methyl acrylate-methacrylic acid copolymers, starch acetate phthalate, cellulose acetate succinate, styrene-maleic acid copolymers, starch polyacetate, cellulose benzoate phthalate, methylcellulose phthalate, ethylhydroxyethylcellulose phthalate, cellulose acetate maleate, hydroxypropylmethylcellulose phthalate, amylose acetate phthalate, poly(vinyl alcohol) phthalate, polyvinyl acetate phthalate, polyvinyl propionate phthalate, polyvinyl butyrate phthalate, polyvinyl acetacetal succinate, vinyl acetate-phthalic anhydride copolymers, styrene-phthalic anhydride copolymers, vinyl methyl ether-maleic anhydride copolymers, ethylene-maleic anhydride copolymers, acrylonitrile-methyl acrylate-maleic anhydride copolymers, butyl acrylate-styrene-maleic anhydride copolymers, styrene-acrylic acid copolymers, butyl acrylate-styrene-acrylic acid copolymers, styrene-acrylic acid copolymers, butyl acrylate-styrene-methacrylic acid copolymers, cellulose propionate phthalate and methyl methacrylate-methacrylic acid copolymers.

Of these, we particularly prefer to use carboxymethylethylcellulose, which contains no ester bonds in its molecule and is highly stable to hydrolysis. It forms a highly stable suspension in the presence of a plasticizer and is particularly useful in aqueous systems. With certain other high polymers which are soluble in intestinal juices, coating may be difficult because of cohesion and/or fusion of suspended particles when using a gear pump, or when stirring or blending the suspension at a high shear rate, or during storage at temperatures exceeding 30° C. Surprisingly, plasticizers which are effective when used in organic solvent-based systems containing carboxymethylethylcellulose as the polymer (such as triacetin, acetylated monoglycerides, polyethylene glycol, castor oil, cetyl alcohol and stearic acid) as well as other materials which have commonly been used as plasticizers (such as propylene glycol and various esters of glycerol with higher fatty acids) resulted in crazing and shrinking of the film formed from aqueous systems and, as a result, the coated preparations obtained were not satisfactory for practical use. On the contrary, the addition of the monoesters or diesters in accordance with the present invention as plasticizers to carboxymethylethylcellulose produced excellent films which were clear and without crazing or observable shrinkage. Practical coating operations also yielded good enteric-coated preparations. Although, as noted above, a wide range of high molecular weight enteric polymers can be used in accordance with the present invention, the invention is of particular value for use with carboxymethylethylcellulose as the polymer of the aqueous coating preparation.

There is no particular limitation on the amount of plasticizer of the invention incorporated in the aqueous suspension and the amount actually chosen will vary, depending upon the natures of the suspension and of the film-forming polymer employed. However, too small an amount will be insufficient to give plasticity, whilst too large an amount may cause inconvenience in handling, because the coated product can stick to the vessel or to other similar products. Accordingly, we normally prefer to employ the plasticizer of the invention in an amount of from 0.2 to 0.5 times the weight of the film-forming enteric polymer.

If desired, various other conventional additives may be incorporated into the aqueous suspension employed in the present invention. Examples of such conventional additives include: other plasticizers; high polymers as a suspending agent for high molecular weight particles and/or the plasticizer; surface active agents; colouring agents; and fillers, such as titanium oxide, talc or barium sulphate. The addition of surface active agents, especially polysorbates such as polysorbate 80, is recommended.

The aqueous suspension of the invention may be prepared by conventional procedures well known for use with conventional suspensions of this type.

The solid preparation to be coated by the process of the invention may be in any form, for example in the form of granules, fine granules, pills, capsules, tablets or powders. These solid preparations may be coated by, for example, spraying or otherwise applying the coating agent to the preparation or by immersing the preparation in the coating agent. Various conventional coating apparatus may be employed to facilitate this, including, for example, a coating granulating apparatus of the centrifugal fluidised type, a pan coating apparatus or a fluidised bed granulating coating apparatus.

After the solid preparation has been coated with the polymer and plasticizer in accordance with the present invention, other conventional procedures may be followed, including glazing, sugar coating or additional coating using another coating agent. Also, of course, the solid preparation may be coated with another coating agent prior to application of the aqueous suspension of the present invention.

The invention is further illustrated by the following non-limiting Examples, in which all parts and percentages are by weight, except where otherwise indicated.

EXAMPLES 1 TO 10

(a) Preparation of carboxymethylethylcellulose fines 450 g of carboxymethylethylcellulose (hereinafter referred to as "CMEC"), manufactured by Freund Industrial Co. Ltd. were suspended in 11 550 g of water. To this suspension were added 1 500 g of a 0.5N aqueous solution of sodium hydroxide to dissolve the CMEC. The solution was screened through a 150 Tyler standard mesh.

To the solution were added 1 500 g of a 0.5N aqueous solution of hydrochloric acid, whilst stirring the mixture under a high rate of shear at room temperature. The mixture was then heated to 80° C. and maintained at that temperature, with stirring, for about 10 minutes, after which it was cooled nearly to room temperature. The CMEC fines thus produced were washed, separated by filtration and dried in an air dryer at 60° C. for 1 hour. The particle size of the CMEC fines thus obtained was approximately $1-2 \times 10^{-6}$ m.

(b) Preparation of casting film

CMEC fines prepared as described in step (a) above were added, in an amount of 10%, to water, after which the ester specified in Table 2 was added in the amount shown in that Table. To certain of the mixtures was also added 0.5% of polysorbate 80 (indicated in Table 2 by "+"), whilst others (indicated by "−") did not have this addition. The mixture was stirred to give an emulsified suspension, which was poured into a dish and allowed to stand at 40° C. for about 20 hours, to evaporate off the water.

The various esters employed in these Examples had the compositions shown in Table 1. The properties of the casting films thus prepared are shown in Table 2.

TABLE 1

| Ester No. | Acid | Monoester content (%) | Diester content (%) |
|---|---|---|---|
| I | Octanoic | 88 | 7 |
| II | Octanoic | 55 | 33 |
| III | Octanoic | 54 | 37 |
| IV | Octanoic | 4 | 81 |
| V | Hexanoic | 94 | 3 |
| VI | Decanoic | 92 | 3 |
| VII | Hexanoic | 64 | 26 |
| VIII | Hexanoic | 50 | 38 |
| IX | Hexanoic | 35 | 50 |
| X | Hexanoic | 5 | 73 |

TABLE 2

| Ex. No. | Ester No. | Amount (%) of ester | Poly- sorb- ate | Film Formation (Note 1) | Film Shrinkage (Note 2) | Film Plasticity (Note 3) |
|---|---|---|---|---|---|---|
| 1 | I | 1 | − | b | a | a |
| | | 2 | − | b−c | b | b |
| | | 3 | − | c | c−b | c |
| | | 1 | + | a | / | / |
| | | 2 | + | b−c | b | c |
| | | 3 | + | c | c−b | c |
| 2 | II | 1 | + | a | / | / |
| | | 2 | + | b−c | b | c |
| | | 3 | + | c | c | c |
| 3 | III | 0.5 | − | a | / | / |
| | | 1 | − | a | / | / |
| | | 1.5 | − | a−b | / | / |
| | | 2 | − | b | / | / |
| | | 2.5 | − | c | b | c |
| | | 3 | − | c | c | c |
| | | 1 | + | a | / | / |
| | | 1.5 | + | b | / | / |
| | | 2 | + | c | c | b |
| | | 2.5 | + | c | c | c |
| | | 3 | + | c | c | d |
| | | 3.5 | + | c | c | d |
| | | 4 | + | c | c | d |
| 4 | IV | 1 | + | a | / | / |
| | | 2 | + | a | / | / |
| | | 3 | + | b | a−b | b |
| 5 | V | 2 | − | c | c | b |
| | | 3 | − | c | c | c |
| | | 2 | + | c | c | b |
| | | 3 | + | c | c | c |
| 6 | VI | 1 | − | a | / | / |
| | | 2 | − | c | b | b |
| | | 3 | − | c | b | c |
| | | 1 | + | a | / | / |
| | | 2 | + | c | b | b |
| | | 3 | + | c | b | b |
| 7 | VII | 3 | + | c | c | c |
| 8 | VIII | 3 | + | c | c | c |
| 9 | IX | 3 | + | c | c | c |
| 10 | X | 3 | + | b−c | b | b |

Notes
1 - The symbols used have the following meanings:
a = no film formed;
b = film formed but crazed;
c = uniform clear film.
2 - The symbols used have the following meanings:
a = the film shrank;
b = the film shrank slightly;
c = no shrinkage.
3 - The symbols used have the following meanings:
a = no plasticity;
b = poor plasticity;
c = good plasticity;
d = excellent plasticity.

In the columns "Shrinkage" and "Plasticity", the symbol "/" means that the properties were not assessed because either no film was formed or the film which formed was of too poor a quality.

Although certain of the plasticizers, in relatively low amounts, gave poor results, comparison of these results with those achieved in Comparative Examples 1-31 (employing plasticizers other than the monoesters and diesters of glycerol with $C_6$-$C_{10}$ acids), the esters of the present invention exhibited far superior film-forming, film shrinkage and plasticity properties to those achieved with the conventional plasticizers. This demonstrates that the esters of the present invention are excellent plasticizers.

EXAMPLE 11

Preparation of casting film

Hydroxypropylmethylcellulose phthalate fines (HP-55 F, manufactured by Shinetsu Kagaku Kogyo K.K.) were added in a proportion of 10% to water, followed by Ester III (whose composition is as defined in Table 1) in the proportion specified in Table 3 and 0.5% of polysorbate 80. The mixture was stirred to give an emulsified suspension, which was then poured into a dish and allowed to stand at 40° C. for about 20 hours, to allow the water to evaporate off. The results achieved are shown in Table 3, in which the symbols used have the same meanings as defined for Table 2.

TABLE 3

| Amount (%) of ester | Poly- sorb- ate | Film properties | | |
|---|---|---|---|---|
| | | Formation | Shrinkage | Plasticity |
| 1 | + | a | / | / |
| 2 | + | b-c | b | b |
| 3 | + | c | c | c |

As with Examples 1-10, it was found that the ester employed was an excellent plasticizer.

EXAMPLE 12

(a) Preparation of bare tablets

In a mortar were thoroughly blended 0.065 part of p-ethoxychrysoidine, a pH indicator, and 6.435 parts of lactose, to prepare a 1 in 100 diluted powder of the indicator. 6.5 parts of this diluted powdery indicator, 81.55 parts of lactose, 20 parts of crystalline cellulose and 20 parts of partially substituted hydroxypropylcellulose (i.e. a hydroxycellulose in which 5-16% of the original hydroxy groups have been replaced by hydroxypropyl groups) were blended in an Henshell mixer, after which 26 parts of a 5% aqueous solution of hydroxypropylcellulose were added and the mixture was kneaded. The kneaded mixture was dried in an air drier at 60° C. for 1 hour and then screened through a 20 Tyler standard mesh screen to give granules. 129.35 parts of these granules and 0.65 parts of magnesium stearate were blended in a V-form mixture, and then the blend was tabletted using a punch of diameter 7.14 mm and depth 9.53 mm into tablets each weighing 130 mg.

(b) Preparation of coating agent

A mixture of 10% CMEC fines prepared as described in Examples 1-10 (a), 3% of Ester III (whose composition is given in Table 1), 0.5% polysorbate 80 and 86.5% purified water was stirred to prepare a coating agent.

(c) Coating

Coating was carried out by placing 500 g of the bare tablets prepared as described in step (a) in a coating pan and then subjecting them to repeated spraying and drying cycles. The inlet temperature of the air employed for the drying cycles was 60° C. The time per cycle was approximately 2 minutes and the rate of spraying per cycle was 5 g of coating agent.

(d) Results 6 tablets which had been spray-coated with 600 g of coating agent per 500 g of bare tablets were shaken in a Pharmacopoeia of Japan Solution No. 1 (simulated gastric juices) on a disk, using a Pharmacopoeia of Japan disintegration tester at 37° C. for 2 hours. No permeation of the solution into the tablets was observed and none of the six tablets showed any release of indicator. The tablets were also shaken in a Pharmacopoeia of Japan Solution No. 2 (simulating intestinal juices) at 37° C. using a Pharmacopoeia of Japan disintegration tester. The average disintegration time for the six tablets was 8 minutes, the individual values being within the range from 7 to 10 minutes. These results indicate that the coating on the tablets was an excellent enteric formulation.

EXAMPLE 13

As described in Example 12, the same bare tablets were spray-coated under the same conditions with the same coating agent in an amount of 750 g of coating agent per 500 g of bare tablets. A dissolution test was run on the coated tablets by the paddle method of the United States Pharmacopoeia at 100 rpm. Measurements were made to determine the extent of release of the indicator incorporated in each tablet. The results are shown in the accompanying drawing, in which the mark x indicates the results of a test in which the bare tablet was poured directly into Pharmacopoeia of Japan Solution No. 2—the tablets instantly released the indicator and disintegrated. The mark o indicates the results with tablets according to the present invention—stirring in Solution No. 1 for 2 hours produced neither the permeation of the solution into the tablets nor release of the indicator. However, when the tablets were transferred to solution No. 2, release of the indicator was observed in approximately the same manner as where the bare tablets were directly poured into the solution, but after a time lag of approximately 10 minutes, indicating that the coated tablets had an excellent enteric coating.

COMPARATIVE EXAMPLES 1-25

CMEC fines prepared in the same way as in Examples 1-10 were added to water in a proportion of 10% to each suspension was added one of the plasticizers specified in Table 4, in the amount specified in that Table. The Table also indicates whether polysorbate 80 was employed—where it was employed, the amount was 0.5% by weight. The mixture was stirred, with heating if necessary, to give an emulsified suspension. This suspension was poured into a dish and then allowed to stand at 40° C. for 20 hours to evaporate off the water.

In each of these Comparative Examples, no film was formed and it was therefore impossible to determine shrinkage or plasticity.

TABLE 4

| Comp. Ex. No. | Plasticizer | Amount (%) | Poly- sorbate |
|---|---|---|---|
| 1 | Decaglycerol pentastearate | 3 | + |
| 2 | Decaglycerol heptastearate | 3 | + |
| 3 | Decaglycerol decastearate | 3 | + |
| 4 | Decaglycerol pentaoleate | 3 | + |
| 5 | Decaglycerol heptaoleate | 3 | + |

TABLE 4-continued

| Comp. Ex. No. | Plasticizer | Amount (%) | Polysorbate |
|---|---|---|---|
| 6 | Decaglycerol decaoleate | 3 | + |
| 7 | Decaglycerol pentaisostearate | 3 | + |
| 8 | Decaglycerol heptaisostearate | 3 | + |
| 9 | Decaglycerol decaisostearate | 3 | + |
| 10 | Glycerol distearate | 3 | + |
| 11 | Glycerol monostearate | 3 | + |
| 12 | Glycerol dioleate | 3 | + |
| 13 | Glycerol monooleate | 3 | + |
| 14 | Glycerol monomyristate | 3 | + |
| 15 | Mybarset 9-40T | 3 | + |
| 16 | Mybarset 7-00 | 3 | + |
| 17 | ODO | 3 | − |
| 18 | ODO | 3 | + |
| 19 | Glycerol trioctanoate | 1 | + |
| 20 | Glycerol trioctanoate | 2 | + |
| 21 | Glycerol trioctanoate | 3 | + |
| 22 | Glycerol triisooctanoate | 3 | + |
| 23 | ODO + triacetin | 1 + 2 | − |
| 24 | Propylene glycol | 3 | − |
| 25 | Polyethylene glycol 6000 | 3 | − |

Mybarset (trade mark) 9-40T is a acetylated monoglyceride whose parent fat is lard, and Mybarset 7-00 is an acetylated monoglyceride whose parent fat is hydrogenated lard, both made by Eastman Chemical products.

ODO is a triglyceride of decanoic acid and octanoic acid, manufactured by Nisshin Seiyu K.K.

COMPARATIVE EXAMPLES 26–31

The procedure of Comparative Examples 1–25 was repeated exactly, except that the plasticizer was employed was triacetin (glycerol triacetate) alone, in the amounts specified in Table 5. This is a widely used plasticizer. The results achieved are shown in Table 5, in which the symbols used are as defined for Table 2. Polysorbate was not used.

TABLE 5

| Comp. Ex. No. | Amount (%) of triacetin | Film properties Formation | Shrinkage | Plasticity |
|---|---|---|---|---|
| 26 | 3 | a | / | / |
| 27 | 3.5 | b | a | b |
| 28 | 4 | b | a | b |
| 29 | 4.5 | b | a | b |
| 30 | 5 | b | a | b |
| 31 | 5.5 | b | a | b |

From the above Table, it can be seen that, although films were achieved in most instances, the films were of poor quality and were quite unsuitable for practical use due to shrinkage and crazing.

We claim:

1. A process for coating a solid pharmaceutical preparation in which an aqueous suspension of a film-forming enteric polymer and a plasticizer therefor is applied to a surface of said preparation and the aqueous phase is removed, wherein the plasticizer is selected from monoesters, diesters and mixtures thereof of glycerol with a saturated aliphatic carboxylic acid having from 6 to 10 carbon atoms.

2. A process as claimed in claim 1, wherein said carboxylic acid is selected from acids having 6, 8 and 10 carbon atoms.

3. A process as claimed in claim 1, wherein said acid is octanoic acid.

4. A process as claimed in claim 1, wherein said polymer is selected from the group consisting of carboxymethylethylcellulose, cellulose acetate phthalate, methyl acrylate-methacrylic acid copolymers, starch acetate phthalate, cellulose acetate succinate, styrene-maleic acid copolymers, starch polyacetate, cellulose benzoate phthalate, methylcellulose phthalate, ethylhydroxyethylcellulose phthalate, cellulose acetate maleate, hydroxypropylmethylcellulose phthalate, amylose acetate phthalate, poly(vinyl alcohol)phthalate, polyvinyl acetate phthalate, polyvinyl propionate phthalate, polyvinyl butyrate phthalate, polyvinyl acetacetal succinate, vinyl acetate-phthalic anhydride copolymers, styrene-phthalic anhydride copolymers, vinyl methyl ether-maleic anhydride copolymers, ethylene-maleic anhydride copolymers, acrylonitrile-methyl acrylate-maleic anhydride copolymers, butyl acrylate-styrene-maleic anhydride copolymers, styrene-acrylic acid copolymers, butyl acrylate-styrene-acrylic acid copolymers, styrene-acrylic acid copolymers, butyl acrylate-styrene-methacrylic acid copolymers, cellulose propionate phthalate and methyl methacrylate-methacrylic acid copolymers.

5. A process as claimed in claim 1, wherein said polymer is selected from the group consisting of carboxymethylethylcellulose and hydroxypropylmethylcellulose phthalate.

6. A process as claimed in claim 1, wherein said polymer is carboxymethylethylcellulose.

7. A process for coating a solid pharmaceutical preparation in which an aqueous suspension of a film-forming enteric polymer and a plasticizer therefor is applied to a surface of said preparation and the aqueous phase is removed, wherein the plasticizer is selected from monoesters, diesters and mixtures thereof of glycerol with a saturated aliphatic carboxylic acid having 6, 8 or 10 carbon atoms, the weight ratio of said plasticizer to said polymer being from 0.2:1 to 0.5:1.

8. A process as claimed in claim 7, wherein said acid is octanoic acid.

9. A process as claimed in claim 7, wherein said polymer is selected from the group consisting of carboxymethylethylcellulose, cellulose acetate phthalate, methyl acrylate-methacrylic acid copolymers, starch acetate phthalate, cellulose acetate succinate, styrene-maleic acid copolymers, starch polyacetate, cellulose benzoate phthalate, methylcellulose phthalate, ethylhydroxyethylcellulose phthalate, cellulose acetate maleate, hydroxypropylmethylcellulose phthalate, amylose acetate phthalate, poly(vinyl alcohol)phthalate, polyvinyl acetate phthalate, polyvinyl propionate phthalate, polyvinyl butyrate phthalate, polyvinyl acetacetal succinate, vinyl acetate-phthalic anhydride copolymers, styrene-phthalic anhydride copolymers, vinyl methyl ether-maleic anhydride copolymers, ethylene-maleic anhydride copolymers, acrylonitrile-methyl acrylate-maleic anhydride copolymers, butyl acrylate-styrene-maleic anhydride copolymers, styrene-acrylic acid copolymers, butyl acrylate-styrene-acrylic acid copolymers, styrene-acrylic acid copolymers, butyl acrylate-styrene-methacrylic acid copolymers, cellulose propionate phthalate and methyl methacrylate-methacrylic acid copolymers.

10. A process as claimed in claim 7, wherein said polymer is selected from the group consisting of carboxymethylethylcellulose and hydropropylmethylcellulose phthalate.

11. A process as claimed in claim 7, wherein said polymer is carboxymethylethylcellulose.

12. A process as claimed in claim 11, wherein said acid is octanoic acid.

13. A process as claimed in claim 10, wherein said acid is octanoic acid.

14. A process as claimed in claim 9, wherein said acid is octanoic acid.

* * * * *